(12) United States Patent  
Pomerantz et al.

(10) Patent No.: US 7,009,762 B2  
(45) Date of Patent: Mar. 7, 2006

(54) GEM MICROSCOPE HAVING A SWIVEL BASE AND A STATIONARY POWER CORD

(75) Inventors: Howard Pomerantz, Newport Beach, CA (US); Sherman Gingerella, Carlsbad, CA (US); Derwin Fritts, Carlsbad, CA (US)

(73) Assignee: Gemological Institute of America, Inc., Carlsbad, CA (US)

( * ) Notice: Subject to any disclaimer, the term of this patent is extended or adjusted under 35 U.S.C. 154(b) by 15 days.

(21) Appl. No.: 10/935,406

(22) Filed: Sep. 7, 2004

(65) Prior Publication Data

US 2005/0094259 A1  May 5, 2005

Related U.S. Application Data

(60) Provisional application No. 60/501,604, filed on Sep. 9, 2003.

(51) Int. Cl.  
*G02B 21/00* (2006.01)  
*G02B 3/00* (2006.01)

(52) U.S. Cl. ................ 359/368; 359/385; 359/809

(58) Field of Classification Search ........ 359/368–398, 359/800–819, 894; 206/6.1, 566; 362/154–156  
See application file for complete search history.

(56) References Cited

U.S. PATENT DOCUMENTS

| | | | | | |
|---|---|---|---|---|---|
| 3,937,320 | A | * | 2/1976 | Chao et al. | 206/216 |
| 3,971,622 | A | * | 7/1976 | Yoshinaga | 359/390 |
| 4,192,580 | A | * | 3/1980 | Meyer | 359/801 |
| 4,285,568 | A | * | 8/1981 | Elgart | 359/390 |
| 5,052,788 | A | * | 10/1991 | Tachibana | 359/391 |
| 5,748,366 | A | * | 5/1998 | Yasunaga et al. | 359/368 |
| 6,322,223 | B1 | | 11/2001 | Smith et al. | 359/871 |
| 6,405,858 | B1 | * | 6/2002 | Gagliardi | 206/6.1 |
| 6,690,512 | B1 | * | 2/2004 | Konopa | 359/391 |
| 6,714,348 | B1 | * | 3/2004 | Dunn | 359/387 |

* cited by examiner

*Primary Examiner*—Thong Q Nguyen  
(74) *Attorney, Agent, or Firm*—DLA Piper Rudnick Gray Cary US LLP; Andrew V. Smith (57) ABSTRACT

A gem microscope includes a base structure that supports the microscope stage, focus column, and optical head. The base structure includes a lower component that receives a power cord; the lower component and the power cord remain stationary when the gem microscope is in use. The base structure also includes an upper component rotatably coupled to the lower component. The upper component can rotate around the lower component to enable convenient sharing of the gem microscope by a number of users. The base structure includes an electrical coupler assembly that maintains an electrical connection (for the gem microscope power supplies) throughout rotation of the gem microscope.

32 Claims, 9 Drawing Sheets

GEM MICROSCOPE HAVING A SWIVEL BASE AND A STATIONARY POWER CORD

CROSS REFERENCE TO RELATED APPLICATIONS

This application claims the benefit of U.S. provisional patent application Ser. No. 60/501,604, filed Sep. 9, 2003, titled GEM MICROSCOPE.

FIELD OF THE INVENTION

The present invention relates generally to gem microscopes. More particularly, the present invention relates to a gem microscope having a swivel base that accommodates different viewing positions.

BACKGROUND OF THE INVENTION

The prior art is replete with different types of microscopes. Gem microscopes are precision instruments that provide specific lighting and viewing conditions for magnified viewing of gems and jewels. Gem microscopes are widely used by gemological researchers, diamond graders, and jewelers. Such microscopes are commercially available from GIA GEM INSTRUMENTS and other manufacturers.

Gem microscopes employ at least one power supply to generate the lighting environment for viewing of the gems. A gem microscope receives power from a standard AC wall supply via a power cord, which enters the gem microscope at its base. Some prior art gem microscopes employ a fixed base structure that serves as a stationary platform for the stage, focus column, and optical head of the microscope. Others may utilize a rotating base having a power cord that rotates with the base. The latter arrangement can be inconvenient when the gem microscope is used in practical environments. For example, in a classroom or laboratory environment, rotation of the gem microscope mentioned above requires additional free space on the table or bench to accommodate the rotation of the power cord. In addition, the sweeping motion of the rotating power cord can cause spills of loose gems, lab equipment, fluids, and/or other objects on the lab table or bench.

BRIEF SUMMARY OF THE INVENTION

A gem microscope according to the present invention incorporates a rotating base that accommodates different user positions. The power cord for the gem microscope remains stationary while the base swivels along with the majority of the gem microscope (including the stage, focus column, and optical head). The gem microscope is suitably configured to maintain the power connection regardless of the rotated position of the base.

The above and other aspects of the present invention may be carried out in one form by a gem microscope having an optical assembly, a stage coupled to the optical assembly, a knuckle joint having a first component and a second component, where the first component is coupled to the stage, and a base coupled to the second component of the knuckle joint. The base has a lower component and an upper component rotatably coupled to the lower component. In operation, the lower base component serves as a stationary foundation for the microscope, and the upper base component (and the rest of the microscope) can rotate to provide convenient viewing by shared users and to reduce clearance, safety, and spillage issues.

BRIEF DESCRIPTION OF THE DRAWINGS

A more complete understanding of the present invention may be derived by referring to the detailed description and claims when considered in conjunction with the following Figures, wherein like reference numbers refer to similar elements throughout the Figures.

DETAILED DESCRIPTION OF A PREFERRED EMBODIMENT

It should be appreciated that the particular implementations shown and described herein are illustrative of the invention and its best mode and are not intended to otherwise limit the scope of the invention in any way. Indeed, for the sake of brevity, conventional aspects of gem microscopes, power supplies, etc. (and the individual operating components of the gem microscopes) may not be described in detail herein.

Figure 1:
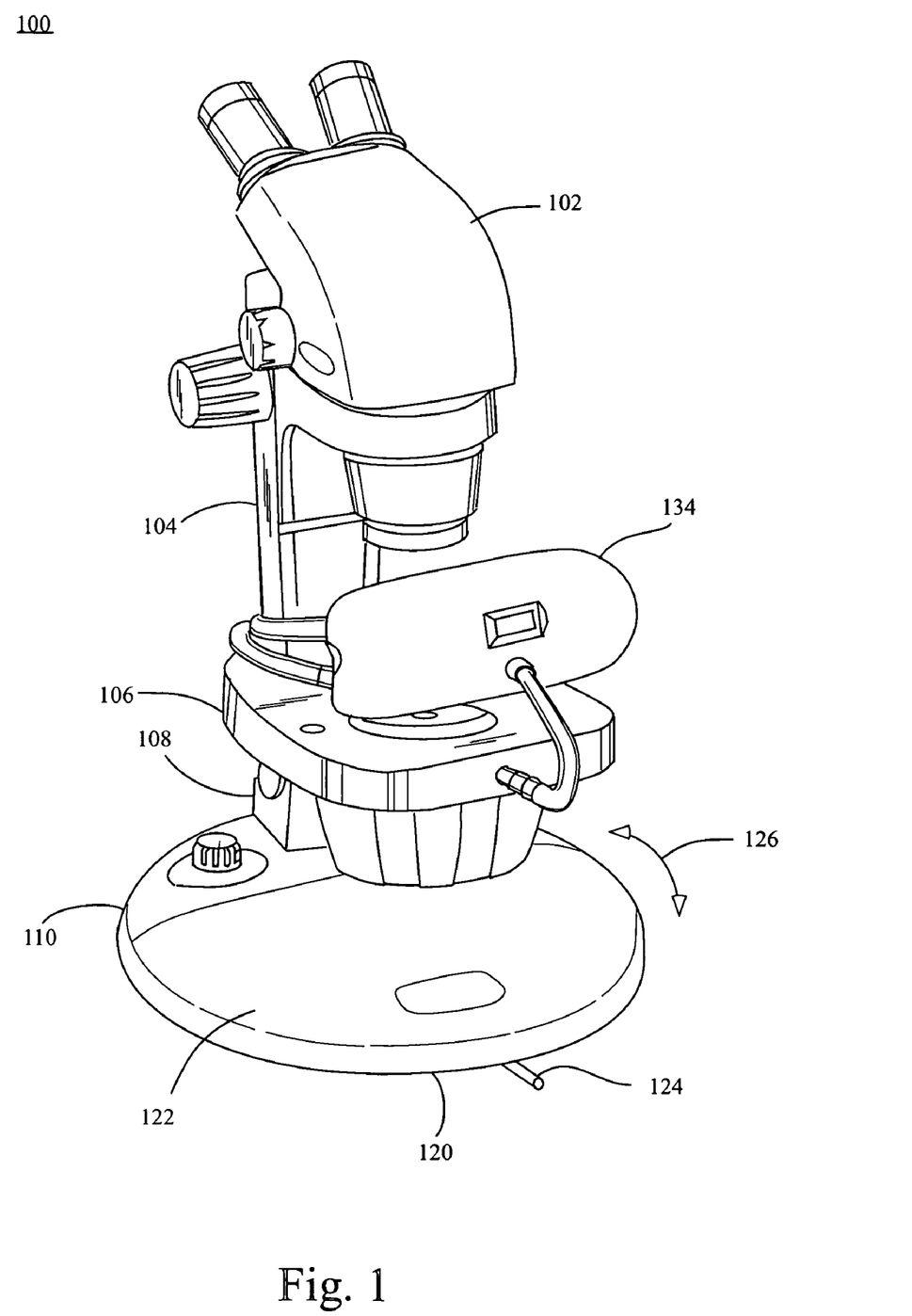
FIG. 1 is a perspective view of a gem microscope that embodies the invention.
Figure 2:
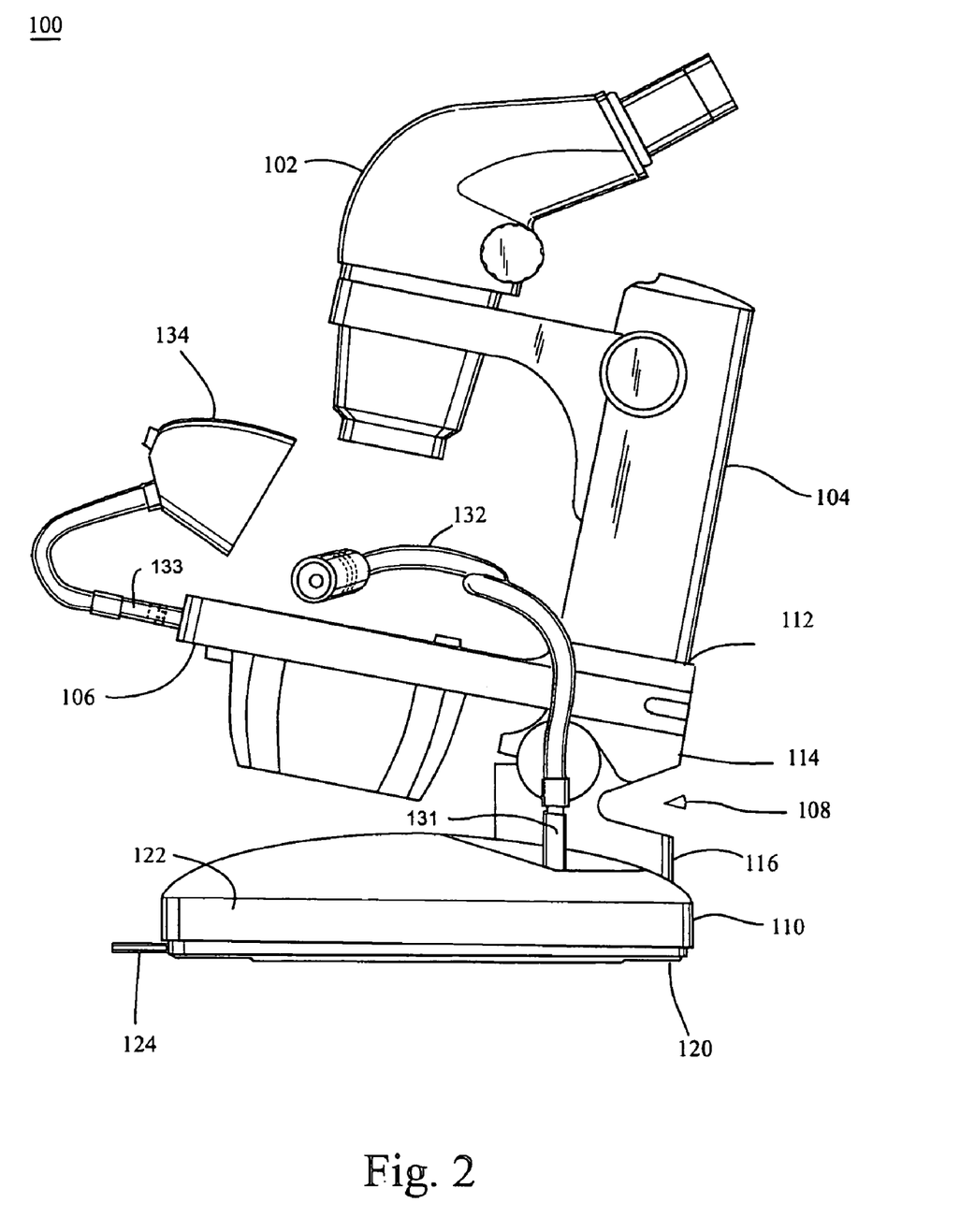
FIG. 2 is a side view of the gem microscope shown in FIG. 1.

FIG. 1 is a perspective view, and FIG. 2 is a side view, of a gem microscope 100 configured in accordance with the invention. Gem microscope 100 generally includes an optical assembly 102, a focus column 104, a stage 106, a knuckle joint 108, and a base structure 110. Optical assembly 102 is coupled to focus column 104, and the two components are suitably configured to allow positional adjustment of optical assembly 102 relative to focus column 104 (along the longitudinal axis of focus column 104). In turn, the lower end 112 of focus column 104 is mounted to stage 106. In this manner, stage 106 is coupled to optical assembly 102. In the example embodiment shown in FIG. 2, lower end 112 is mounted to stage 106 near knuckle joint 108.

Knuckle joint 108 includes at least two components: a first component 114 and a second component 116. As shown in FIG. 2, first component 114 is suitably coupled to stage 106, while second component 116 is suitably coupled to base structure 110. First component 114 and second component 116 are coupled together to form a hinge that facilitates tilt adjustments for gem microscope 100. As described in more detail below, in the practical embodiment, second component 116 is mounted to an upper component 118 (see FIGS. 3–5) of base structure 110.

Base structure 110 generally includes upper component 118, a lower component 120 and a cover 122. As shown in FIG. 2, cover 122 is configured to envelop upper component 118 (not shown) and at least a portion of lower component 120. In the illustrated embodiment, base structure 110 receives a power cord 124 that provides operating power to gem microscope 100. More specifically, power cord 124 is received by lower component 120 of base structure 110. Lower component 120 is configured to provide a stationary foundation for gem microscope 110. In operation, gem microscope 110 should rest on a stable and flat surface, e.g., a table or a laboratory work station surface. In accordance with one practical embodiment, upper component 118 of base structure 110 is rotatably coupled to lower component 120. In FIG. 2, upper component 118 rotates about a centered vertical axis such that it rotates in the horizontal plane. The direction of rotation is indicated by the curved arrow 126 depicted in FIG. 1. In one embodiment, base structure 110 is configured to accommodate 360 degree rotation of upper component 118 relative to lower component 120. In another embodiment, base structure 110 is configured to limit rotation of upper component 118 relative to lower component 120. For example, base structure 110 may restrict the rotation to 270 degrees, 300 degrees, or any suitable angle of rotation.

Figure 3:
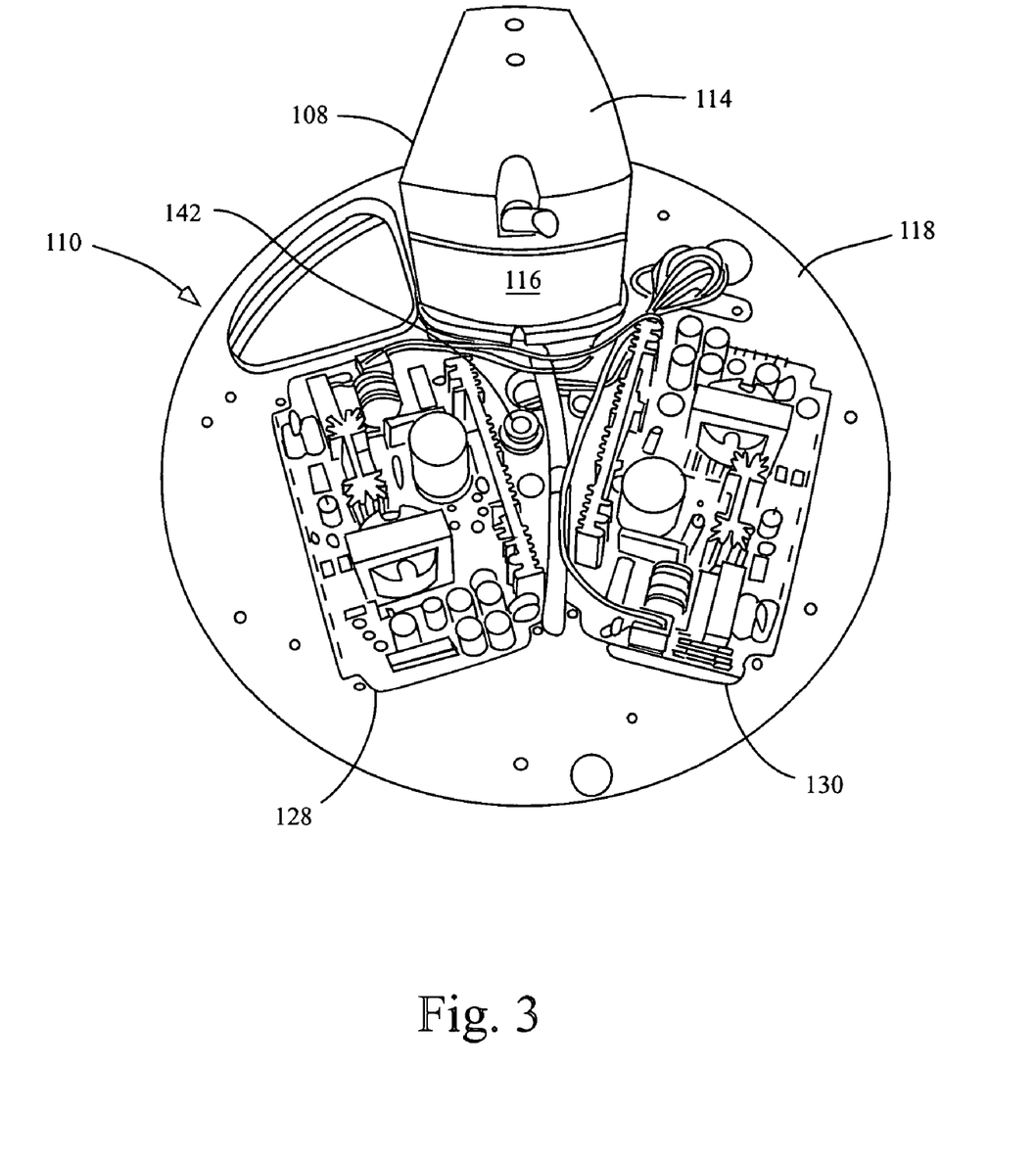
FIG. 3 is a top perspective view of a base assembly configured in accordance with a first embodiment of the invention.
Figure 4:
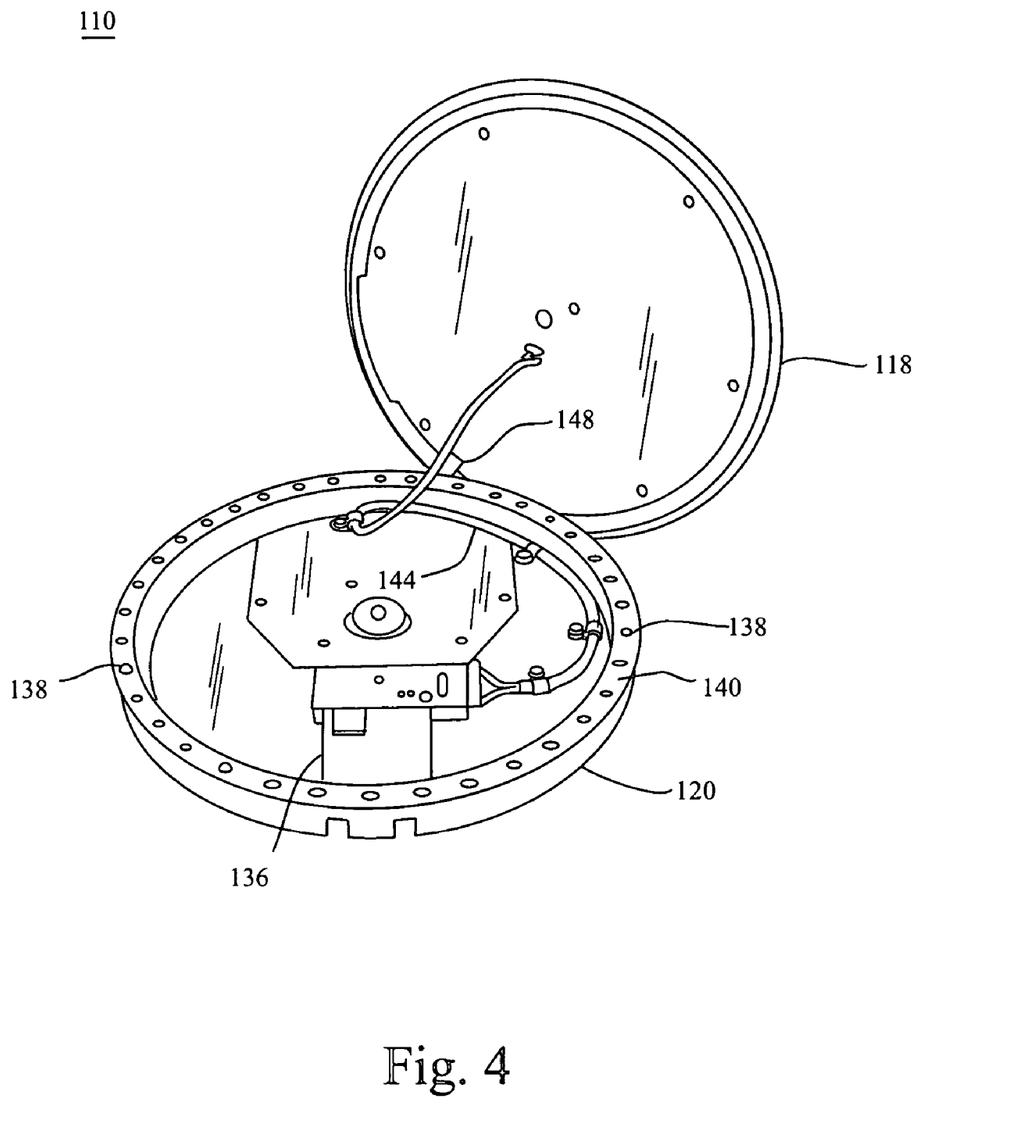
FIG. 4 is a perspective view of the base assembly shown in FIG. 3 in a partially disassembled state.
Figure 5:
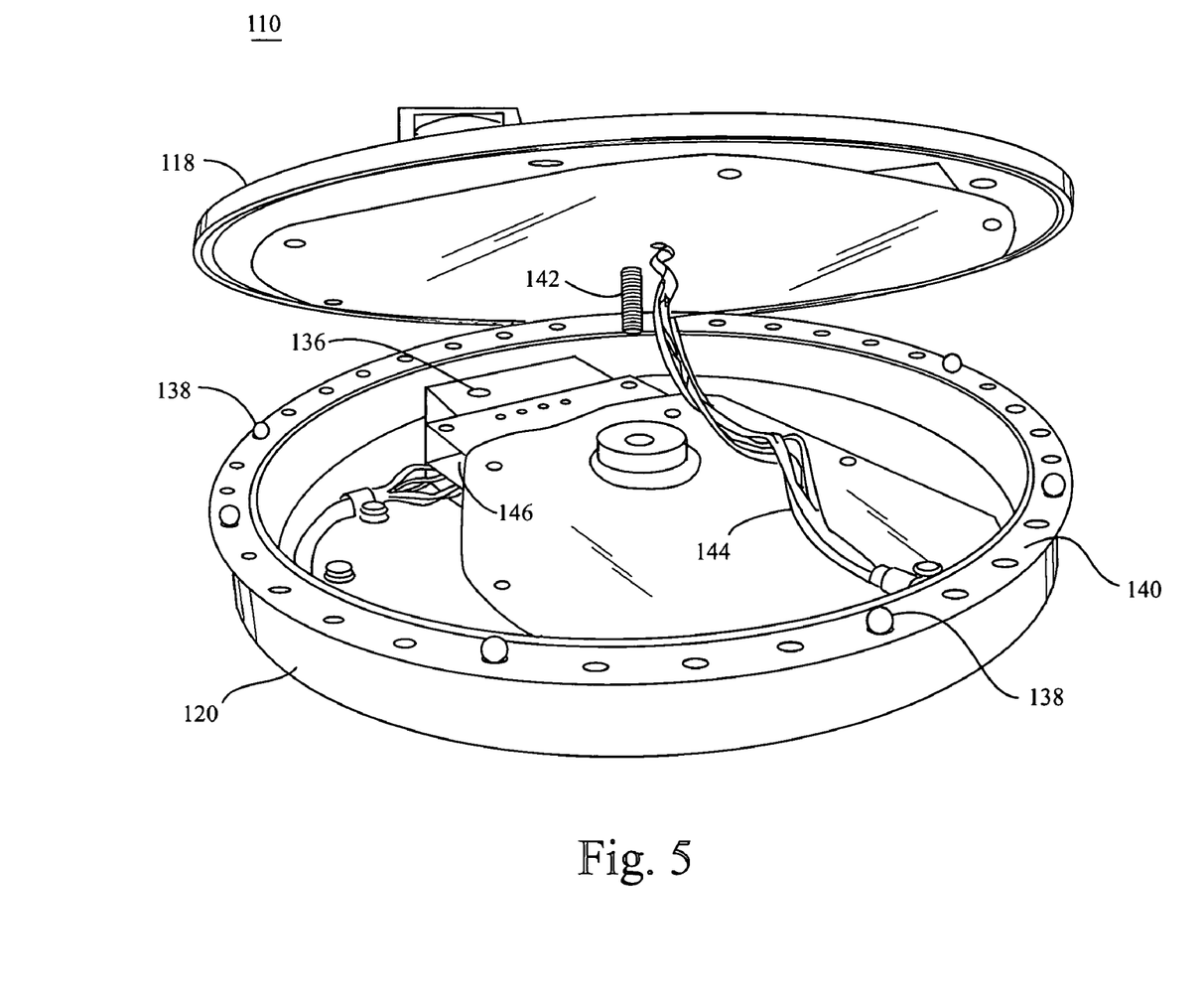
FIG. 5 is another perspective view of the base assembly shown in FIG. 3 in a partially disassembled state.

FIGS. 3–5 are different views showing the details of one example base structure 110 that is suitable for use with gem microscope 100. In these views, cover 122 has been removed. As shown in FIG. 3, second component 116 of knuckle joint 108 is coupled to upper component 118 of base structure 110. Accordingly, in this embodiment, knuckle joint 108, stage 106, focus column 104, and optical assembly 102 all rotate along with upper component 118. Also shown in FIG. 3 are two power supplies 128/130 mounted on the top surface of upper component 118. When installed, cover 122 protects power supplies 128/130 and hides them from view. Power supplies 128/130 can be utilized for dark field illumination, to power lighting fixtures 132/134 (see FIGS. 1 and 2), and/or to power other accessories on gem microscope 100.

Power supplies 128/130 are driven by current supplied by power cord 124 (which in turn obtains current from any suitable source, e.g., a standard 120 V household supply or standard 220 V supply). In the example embodiment, lower component 120 of base structure 110 includes a power cord receptacle 136 that receives power cord 124. As shown, power cord receptacle 136 may be integrated with lower component 120. Power cord receptacle 136 may be configured to mate with a modular end of power cord 124, or it may be configured for permanent attachment to power cord 124. Notably, power cord 124 remains stationary when upper component 118 of base structure 110 rotates relative to lower component 120 of base structure 110.

Power supplies 128/130 are connected to power cord receptacle 136 via a suitably configured electrical coupler assembly. The electrical coupler assembly is configured to maintain an electrical connection between power cord receptacle 136 and power supplies 128/130 throughout rotation of base structure 110. Several different implementations of the electrical coupler assembly are described in detail below. In accordance with one practical embodiment, one power supply is used for the dark field illumination (which occurs in the light bowl below stage 106), and the other power supply delivers power to accessory lighting fixtures such as an overhead lamp and/or an LED illuminator.

In accordance with a preferred embodiment, accessories are coupled to the microscope using special custom made electrical connectors 131 and 133. These connectors may serve to couple different type of accessories to the microscope such as, but not limited to, overhead light 134 and LED light source 132, as shown in FIG. 2. The accessories connector 131 and 133 are preferably used for transferring low voltage (e.g., 0–50 VDC) using a single pin for positive with ground being conducted through the connector material. The connectors 131 and 133 provide flexibility in accessory positioning and have locking wedges. In a preferred embodiment of the microscope 100, there are 3 connectors including 1 connector 131 coupled to the base 110 and 2 connectors coupled to the stage. Thus, 3 accessories may be connected to the microscope 100 and operated at the same time. In an alternative embodiment, either or both of the lighting fixtures 132/134 may be substituted with a light output coupling mechanism that may be optically coupled to a LED light source disposed in the lower component 120, wherein light may be piped to the upper component notwithstanding the relative rotational positions of the lower and upper components 120/118, and light is then guided via fiber optics for illuminating the stage.

In the example embodiment, upper component 118 of base structure 110 glides on a plurality of bearings 138 (see FIG. 4 and FIG. 5) located between upper component 118 and lower component 120 of base structure 110. The upper lip of lower component 120 includes a first bearing channel formed therein, and the edge around the bottom surface of upper component 118 includes a second bearing channel formed therein. When base structure 110 is assembled, bearings 138 ride between upper component 118 and lower component 120 within the first and second bearing channels. Base structure 110 may also include a bearing race 140 having a plurality of holes formed therein for receiving bearings 138. Bearing race 140 maintains the relative spacing of bearings 138 within the first and second bearing channels. As shown in FIG. 5, upper component 118 is coupled to lower component 120 with a bolt 142. The top of bolt 142 is shown in FIG. 3. During assembly, bolt 142 is tightened to sandwich bearings 138 within the two bearing channels, while maintaining enough play to allow free movement of bearings 138. This arrangement facilitates smooth and free rotation of upper component 118 relative to lower component 120.

The embodiment shown in FIGS. 3–5 employs a wire harness 144 as the electrical coupler assembly between power cord receptacle 136 and power supplies 128/130. In this example, wire harness 144 includes six conductors: each power supply 128/130 has a hot conductor, a neutral conductor, and a safety ground conductor. Wire harness 144 includes a suitably configured plug or socket 146 for connection to power cord receptacle 136. Wire harness 144 can be located between upper component 118 and lower component 120 (see FIG. 5) and routed through a hole formed within upper component 118. The individual wires in wire harness 144 are routed to power supplies 128/130, where the appropriate connections are made.

Wire harness 144 contains sufficient slack to prevent binding and twisting during rotation of base structure 110. In the example embodiment, rotation of upper component 118 is limited in both directions by a stop pin 148 (see FIG. 4) that protrudes from the bottom surface of upper component 118. When base structure 110 is assembled, stop pin 148 extends into the cavity defined by lower component 120, and contacts the sides of power cord receptacle 136 to limit rotation of upper component 118. Stop pin 148 restricts rotation of upper component 118 to approximately 320 degrees, thus ensuring that wire harness 144 does not become tangled or overly twisted within base structure 110.

Figure 6:
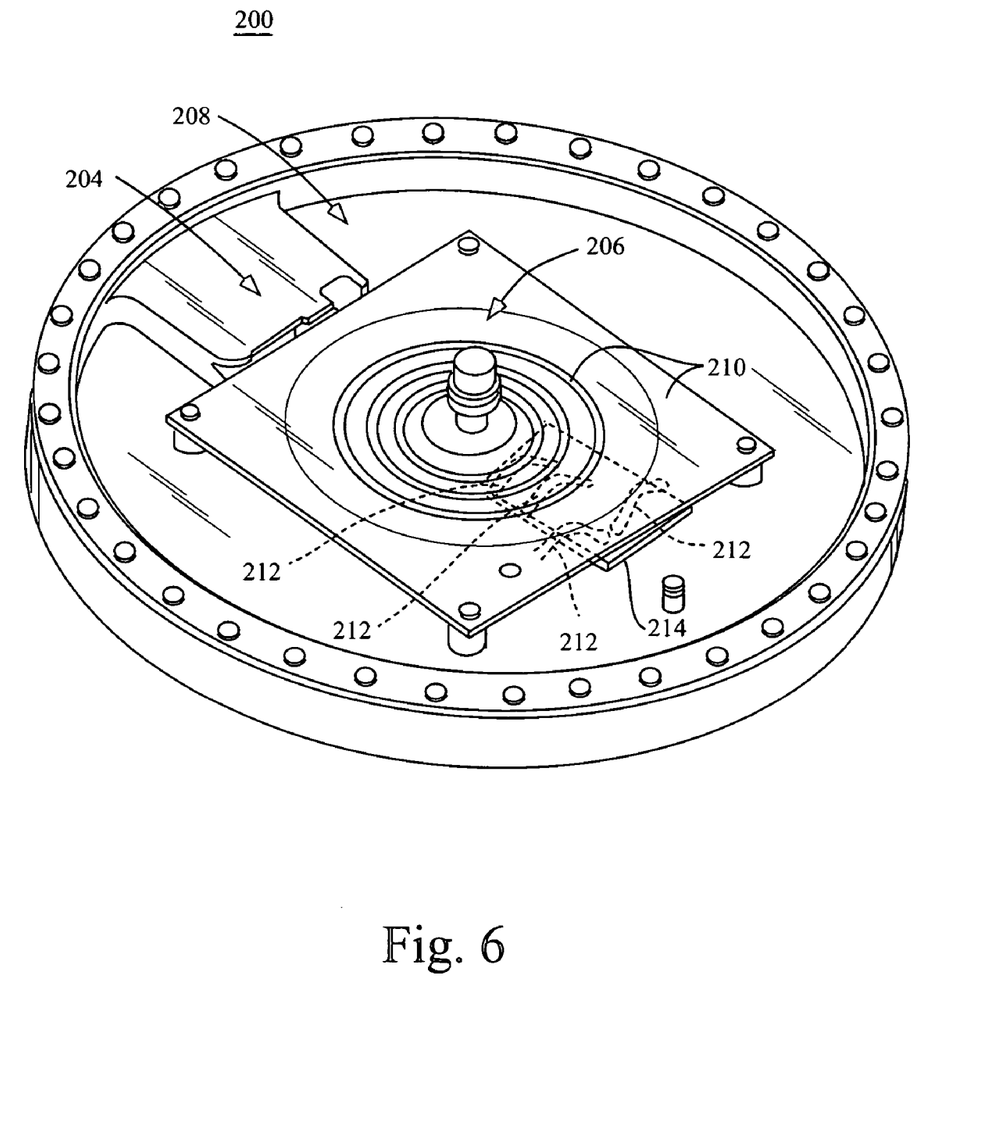
FIG. 6 is a perspective view of a lower base assembly configured in accordance with a second embodiment of the invention.
Figure 7:
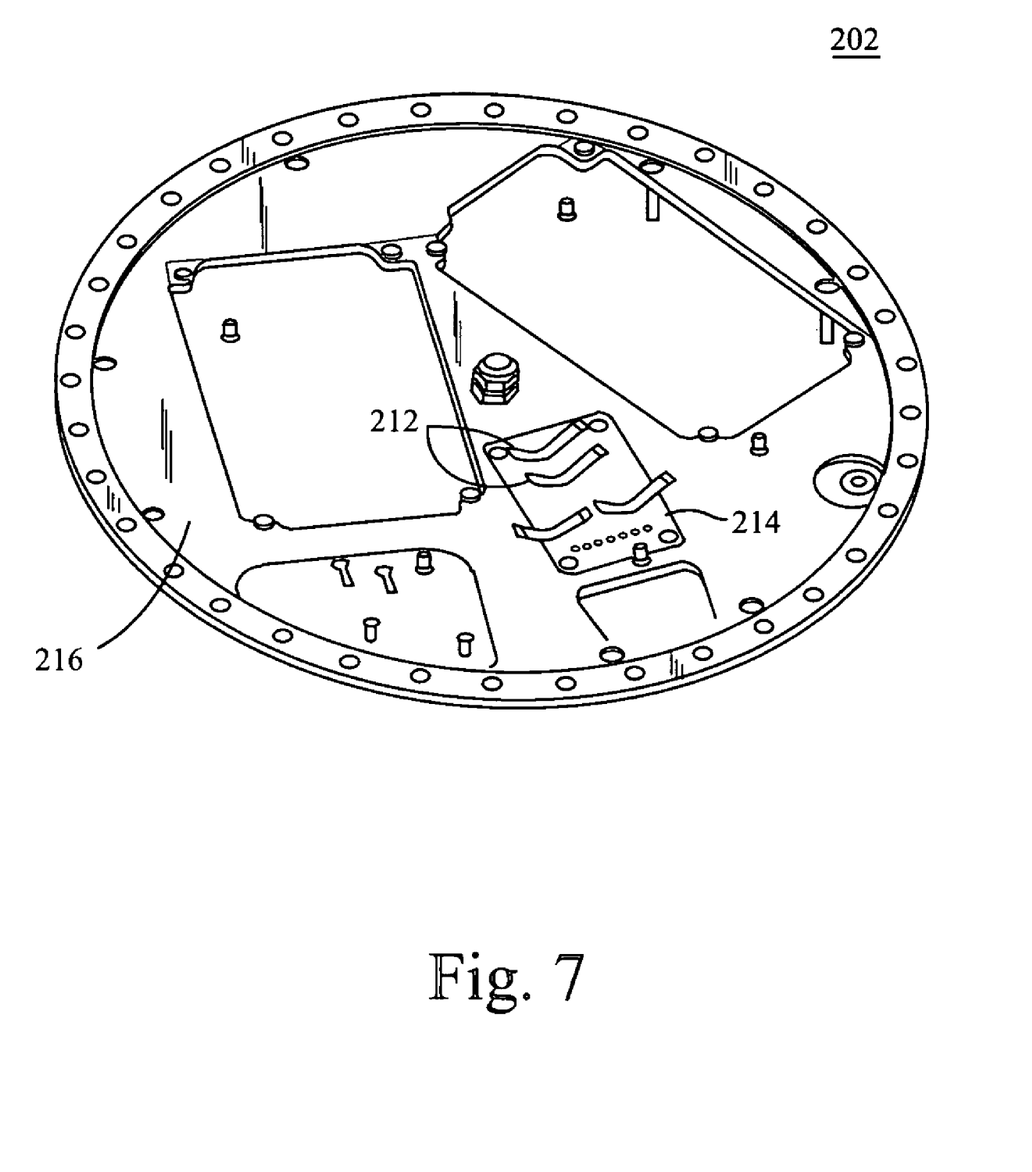
FIG. 7 is a perspective view of an upper base assembly configured in accordance with the second embodiment of the invention.

In accordance with an alternate embodiment, the electrical coupler assembly comprises horizontal slip rings that allow free 360 degree rotation of upper component 118 relative to lower component 120. FIG. 6 is a perspective view of a lower component 200 of a base structure that employs a horizontal slip ring arrangement. FIG. 6 also schematically illustrates how the power cord receptacle 204 and stop pin 148 (not shown in FIG. 6, but see FIG. 4) serve to prevent full 360 degree rotation of the upper component relative to the lower component, instead limiting the relative rotational movement to approximately 320 degrees in the embodiment shown. Alternatively, the power cord receptacle could be narrowed to permit still greater relative rotational movement above 320 degrees. The system may be configured to allow full 360 degree rotational freedom either by permanently or selectively removing or re-positioning the stop pin 148, or by re-shaping the power cord receptacle 204 so as to permanently or selectively not impede the movement of stop pin 148. FIG. 7 is a perspective view of an upper component 202 compatible with lower component 200. FIG. 7 is a perspective view of the bottom surface of upper component 202.

Lower component 200 includes a power cord receptacle 204 as described above in connection with gem microscope 100. Power cord receptacle 204 is electrically connected to a first power transfer board 206, which is connected to the surface 208 of lower component 200. Although hidden from view in FIG. 6, the hot, neutral, and safety ground connections from power cord receptacle 204 are connected to respective conductive traces 210 formed on first power transfer board 206. These traces 210 maintain contact with corresponding conductive contacts 212 located on upper component 202. FIG. 6 depicts contacts 212 as positioned when upper component 202 is coupled to lower component 200. Notably, contacts 212 maintain electrical contact with traces 210 throughout rotation of the base structure. Traces 210 are preferably formed as continuous circles to enable unlimited rotation in either direction.

Upper component 202 includes a second power transfer board 214, upon which contacts 212 are mounted. Second power transfer board 214 is connected to upper component 202 such that contacts 212 protrude from the bottom surface 216 of upper component 202. Although hidden from view in FIG. 7, the opposite side of second power transfer board 214 provides terminals or connection points for hot, neutral, and safety ground conductors that are then routed to one or more power supplies of the gem microscope.

Figure 8:
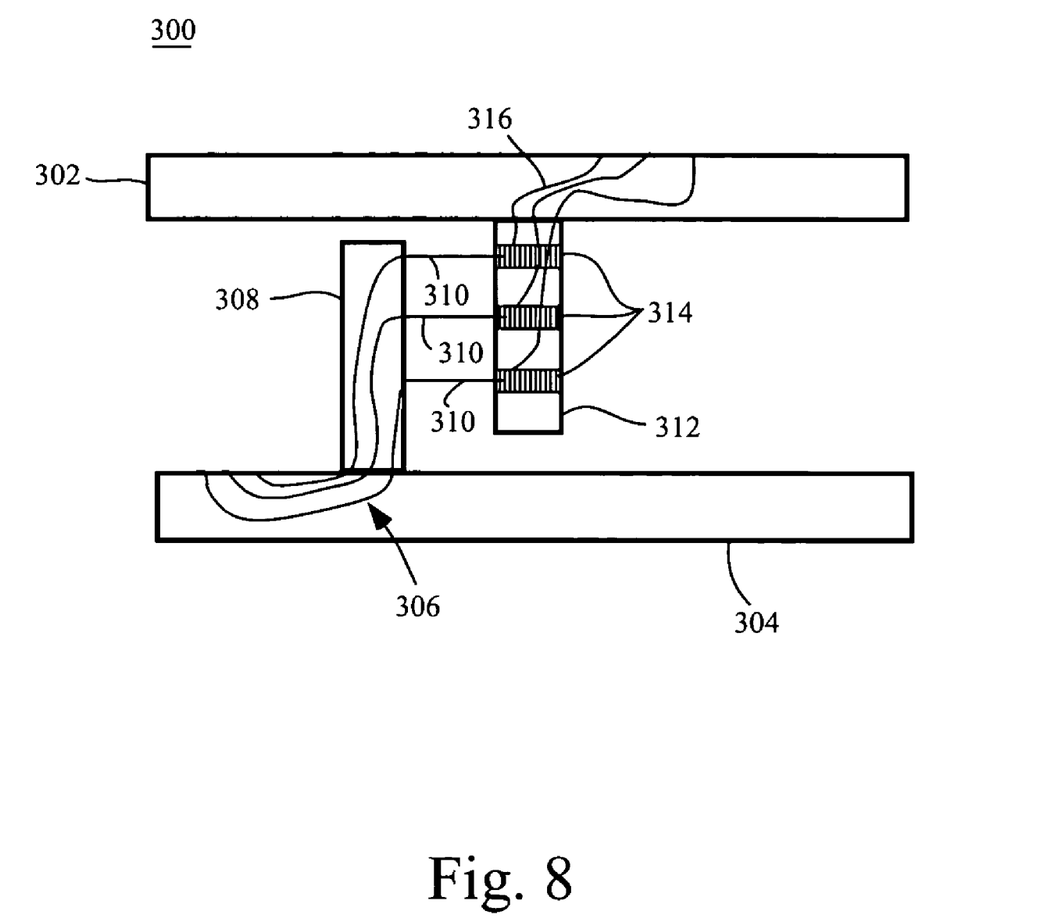
FIG. 8 is a schematic representation of a base assembly configured in accordance with a third embodiment of the invention.

In accordance with another alternate embodiment, the electrical coupler assembly comprises vertical slip rings that allow free 360 degree rotation of the upper base component relative to the lower base component. In this regard, FIG. 8 is a schematic representation of a base structure 300 that incorporates vertical slip rings. Base structure 300 includes an upper component 302 capable of free rotation relative to a lower component 304. As described above, lower component 304 may include a power cord receptacle (not shown) or other suitable means for providing operating power to the gem microscope. The hot, neutral, and safety ground wires for lower component 304 are identified by reference number 306. These wires may be routed through or up a post 308 to a corresponding number of electrical contacts 310 (e.g., pins, brushes, or the like).

Upper component 302 may include a round post 312 having conductive traces 314 formed thereon. Electrical contacts 310 maintain contact with the respective traces 314 throughout rotation of upper component 302 relative to lower component 304. Conductive traces 314 are connected to wires or other conductors 316 that are routed to one or more power supplies used by the gem microscope.

Figure 9:
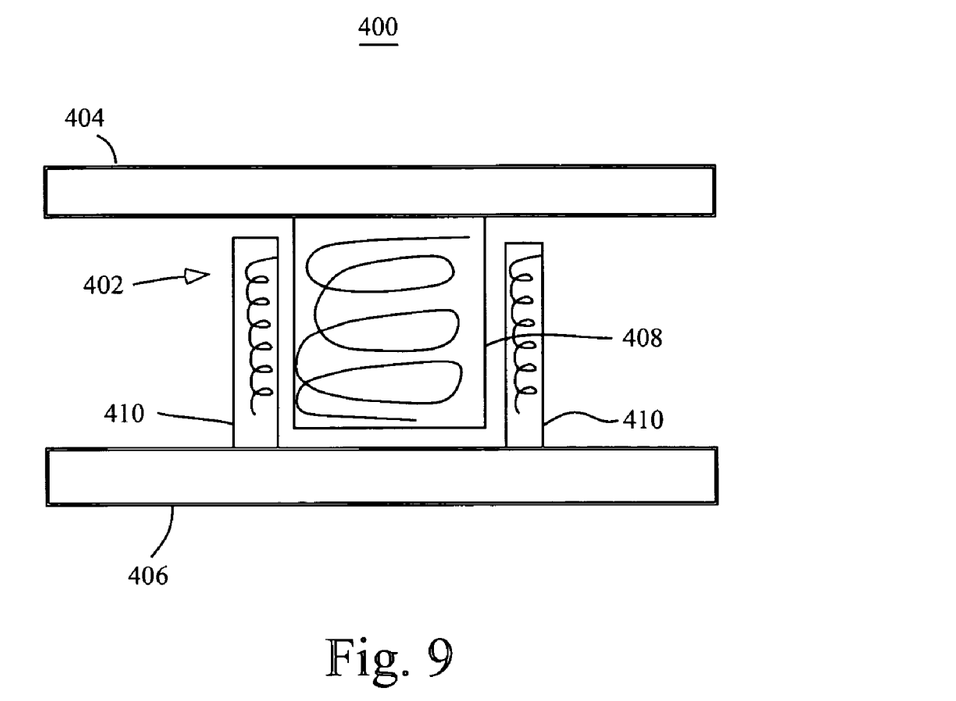
FIG. 9 is a schematic representation of a base assembly configured in accordance with a fourth embodiment of the invention.

In accordance with another alternate embodiment, the electrical coupler assembly comprises a vertically oriented transformer that allows free 360 degree rotation of the upper base component relative to the lower base component. In this regard, FIG. 9 is a schematic representation of a base structure 400 that incorporates a vertical transformer 402. Base structure 400 includes an upper component 404 capable of free rotation relative to a lower component 406. As described above, lower component 406 may include a power cord receptacle (not shown) or other suitable means for providing operating power to the gem microscope. Upper component 404 includes a first transformer coil 408 (e.g., an internal coil), and lower component 406 includes a second transformer coil 410 (e.g., an external coil). In FIG. 9, the coils are shown in cross section. Second coil 410 receives current from the source via the power cord receptacle, and transformer 402 induces current in first coil 408 for use with one or more power supplies.

Figure 10:
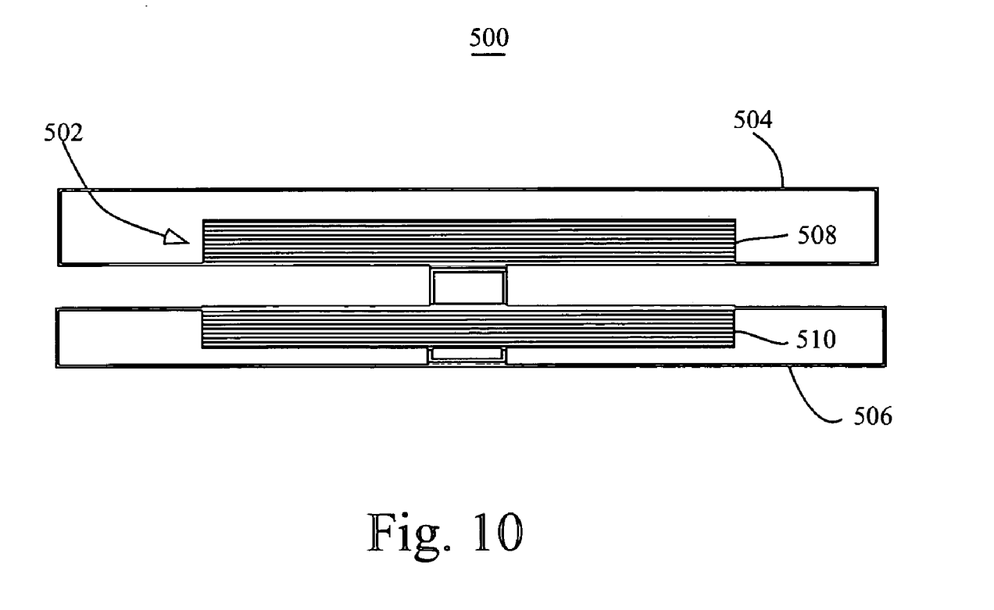
FIG. 10 is a schematic representation of a base assembly configured in accordance with a fifth embodiment of the invention.

In accordance with yet another alternate embodiment, the electrical coupler assembly comprises a horizontally oriented transformer that allows free 360 degree rotation of the upper base component relative to the lower base component. In this regard, FIG. 10 is a schematic representation of a base structure 500 that incorporates a horizontal transformer 502. Base structure 500 includes an upper component 504 capable of free rotation relative to a lower component 506. As described above, lower component 506 may include a power cord receptacle (not shown) or other suitable means for providing operating power to the gem microscope. Upper component 504 includes a first transformer coil 508, and lower component 506 includes a second transformer coil 510. In FIG. 10, the coils are shown in cross section. Second coil 510 receives current from the source via the power cord receptacle, and transformer 502 induces current in first coil 508 for use with one or more power supplies.

Alternative electrical coupling methods and techniques, such as capacitive coupling, may also be employed by a gem microscope to facilitate free rotation as described herein.

The various embodiments described above utilize a rotating base structure having a stationary power supply cord. Alternatively, a gem microscope according to the invention may employ a fixed base structure having a stationary power cord in conjunction with a rotating component that accommodates rotation of the microscope stage and optical assembly relative to the base structure. Referring again to FIG. 2, such a rotating component preferably includes a first element coupled to stage 106 and a second element coupled to base structure 110. For example, the rotating component can be implemented in knuckle joint 108. Alternatively, the rotating component can be realized as one or more parts that are connected between knuckle joint 108 and stage 106 and/or between knuckle joint 108 and base structure 110. Such an embodiment may also employ a suitably configured electrical coupler assembly (as described above) to accommodate rotation of the gem microscope.

The present invention has been described above with reference to a preferred embodiment. However, those skilled in the art having read this disclosure will recognize that changes and modifications may be made to the preferred embodiment without departing from the scope of the present invention. These and other changes or modifications are intended to be included within the scope of the present invention, as expressed in the following claims.

What is claimed is:

1. A gem microscope comprising:
    an optical assembly;
    a stage coupled to said optical assembly;
    a knuckle joint having a first component and a second component, said first component being coupled to said stage; and
    a base coupled to said second component, said base having a lower component and an upper component rotatably coupled to said lower component.

2. A gem microscope according to claim 1, wherein said second component of said knuckle joint is coupled to said upper component of said base.

3. A gem microscope according to claim 1, wherein said lower component of said base comprises a power cord receptacle.

4. A gem microscope according to claim 3, further comprising at least one power supply connected to said power cord receptacle.

5. A gem microscope according to claim 4, wherein said at least one power supply is mounted to said upper component of said base.

6. A gem microscope according to claim 4, further comprising an electrical coupler assembly configured to maintain an electrical connection between said power cord receptacle and said at least one power supply throughout rotation of said base.

7. A gem microscope according to claim 6, wherein said electrical coupler assembly comprises:
    a first power transfer board connected to said lower component of said base, said first power transfer board having a number of continuous conductive traces formed therein; and
    a second power transfer board connected to said upper component of said base, said second power transfer board having a number of conductive contacts configured to maintain contact with said number of conductive traces throughout rotation of said base.

8. A gem microscope according to claim 6, wherein said electrical coupler assembly comprises vertical slip rings.

9. A gem microscope according to claim 6, wherein said electrical coupler assembly comprises a vertically oriented transformer.

10. A gem microscope according to claim 6, wherein said electrical coupler assembly comprises a horizontally oriented transformer.

11. A gem microscope according to claim 1, wherein said base is configured to accommodate at least approximately 320 degree rotation of said upper component relative to said lower component.

12. A gem microscope according to claim 1, further comprising a LED light source disposed in the lower component, an optical coupling and a light output coupling mechanism, wherein the optical coupling is configured to permit light to be generated by the LED light source in the lower component and to be guided via fiber optics to the light output coupling mechanism for illuminating the stage.

13. A gem microscope comprising:
    (a) an optical assembly;
    (b) a stage coupled to said optical assembly for disposing a gemstone at an object position of said optical assembly; and
    (c) a base structure for the gem microscope, said base structure comprising:
        a lower component configured to provide a stationary foundation for said gem microscope;
        an upper component rotatably coupled to said lower component; and
        a power cord receptacle integral to said lower component.

14. A gem microscope according to claim 13, further comprising at least one power supply connected to said power cord receptacle.

15. A gem microscope according to claim 14, further comprising an electrical coupler assembly configured to maintain an electrical connection between said power cord receptacle and said at least one power supply throughout rotation of said base.

16. A gem microscope according to claim 13, wherein said upper component is configured for coupling to a knuckle joint.

17. A base structure for a gem microscope, said base structure comprising:
    a lower component configured to provide a stationary foundation for said gem microscope;
    an upper component rotatably coupled to said lower component;
    a power cord receptacle integral to said lower component; and
    at least one power supply connected to said power cord receptacle, and
    wherein said at least one power supply is mounted to said upper component.

18. A base structure for a gem microscope, said base structure comprising:
    a lower component configured to provide a stationary foundation for said gem microscope;
    an upper component rotatably coupled to said lower component;
    a power cord receptacle integral to said lower component; and
    at least one power supply connected to said power cord receptacle, and
    an electrical coupler assembly configured to maintain an electrical connection between said power cord receptacle and said at least one power supply throughout rotation of said base, and
    wherein said electrical coupler assembly comprises:
        a first power transfer board connected to said lower component of said base, said first power transfer board having a number of continuous conductive traces formed therein; and
        a second power transfer board connected to said upper component of said base, said second power transfer board having a number of conductive contacts configured to maintain contact with said number of conductive traces throughout rotation of said base.

19. A base structure according to claim 18, wherein said electrical coupler assembly comprises vertical slip rings.

20. A base structure according to claim 18, wherein said electrical coupler assembly comprises a vertically oriented transformer.

21. A base structure according to claim 18, wherein said electrical coupler assembly comprises a horizontally oriented transformer.

22. A base structure for a gem microscope, said base structure comprising:
    a lower component configured to provide a stationary foundation for said gem microscope;
    an upper component rotatably coupled to said lower component; and
    a power cord receptacle integral to said lower component, wherein said upper component and said lower component are configured to accommodate at least 320 degree rotation.

23. A base structure for a gem microscope, said base structure comprising:
   a lower component configured to provide a stationary foundation for said gem microscope;
   an upper component rotatably coupled to said lower component; and
   a power cord receptacle integral to said lower component; and
   at least one power supply connected to said cower cord receptacle, and further comprising a LED light source disposed in the lower component, an optical coupling and a light output coupling mechanism, wherein the optical coupling is configured to permit light to be generated by the LED light source in the lower component and to be guided via fiber optics to the light output coupling mechanism for illuminating the stage.

24. A base structure for a gem microscope, said base structure comprising:
   a lower component configured to provide a stationary foundation for said gem microscope;
   an upper component rotatably coupled to said lower component; and
   a power cord receptacle integral to said lower component, and further comprising a cover configured to envelop said upper component and at least a portion of said lower component.

25. A gem microscope comprising:
   a base;
   a stage;
   an optical assembly coupled to said stage; and
   a rotating component having a first element coupled to said stage and a second element coupled to said base, said rotating component being configured to accommodate rotation of said stage and said optical assembly relative to said base,
   wherein a lower component of said base comprises a power cord receptacle, and
   wherein said power cord receptacle is connected to at least one power supply that is mounted to an upper component of said base.

26. A gem microscope according to claim 25, further comprising an electrical coupler assembly configured to maintain an electrical connection between said power cord receptacle and said at least one power supply throughout rotation of said base.

27. A gem microscope according to claim 26, wherein said electrical coupler assembly comprises:

a first power transfer board connected to a lower component of said base, said first power transfer board having a number of continuous conductive traces formed therein; and a second power transfer board connected to an upper component of said base, said second power transfer board having a number of conductive contacts configured to maintain contact with said number of conductive traces throughout rotation of said base.

28. A gem microscope according to claim 27, wherein said electrical coupler assembly comprises vertical slip rings.

29. A gem microscope according to claim 27, wherein said electrical coupler assembly comprises a vertically oriented transformer.

30. A gem microscope according to claim 27, wherein said electrical coupler assembly comprises a horizontally oriented transformer.

31. A gem microscope comprising:
   a base;
   a stage;
   an optical assembly coupled to said stage; and
   a rotating component having a first element coupled to said stage and a second element coupled to said base, said rotating component being configured to accommodate rotation of said stage and said optical assembly relative to said base, and wherein said base is configured to accommodate at least approximately 320 degree rotation of said upper component relative to said lower component.

32. A gem microscope comprising:
   a base;
   a stage;
   an optical assembly coupled to said stage; and
   a rotating component having a first element coupled to said stage and a second element coupled to said base, said rotating component being configured to accommodate rotation of said stage and said optical assembly relative to said base, and further comprising a LED light source disposed in the lower component, an optical coupling and a light output coupling mechanism, wherein the optical coupling is configured to permit light to be generated by the LED light source in the lower component and to be guided via fiber optics to the light output coupling mechanism for illuminating the stage.

* * * * *